United States Patent [19]

Veney

[11] 4,395,424

[45] * Jul. 26, 1983

[54] COSMETIC COMPOSITION AND METHOD OF MAKING THE SAME

[76] Inventor: Ruby G. Veney, 4520 Pine St., Philadelphia, Pa. 19143

[ * ] Notice: The portion of the term of this patent subsequent to Mar. 10, 1998, has been disclaimed.

[21] Appl. No.: 236,989

[22] Filed: Feb. 23, 1981

Related U.S. Application Data

[63] Continuation-in-part of Ser. No. 21,551, Mar. 19, 1979, Pat. No. 4,255,452.

[51] Int. Cl.³ ............................................. A61K 47/00
[52] U.S. Cl. .................................... 424/359; 424/365
[58] Field of Search ........................................ 424/359

[56] References Cited

U.S. PATENT DOCUMENTS

| | | | |
|---|---|---|---|
| 3,959,491 | 5/1976 | Young et al. | 424/359 |
| 4,087,555 | 5/1978 | Barnett et al. | 424/357 |
| 4,129,645 | 12/1978 | Barnett et al. | 424/359 |
| 4,209,503 | 6/1980 | Shah et al. | 424/359 |

FOREIGN PATENT DOCUMENTS 1949207  4/1971  Fed. Rep. of Germany ...... 424/359

OTHER PUBLICATIONS

Pharmaceutical Formulas, 1946, vol. 2, pp. 80, 83, 85 and 108 (10th ed.).

*Primary Examiner*—Dale R. Ore
*Attorney, Agent, or Firm*—Steele, Gould & Fried

[57] ABSTRACT

A cosmetic cream preparation for cleansing, smoothing and moisturizing the skin basically comprising a mixture with water of non-fat dry milk solids, witch hazel and olive oil. An emollient and preservative may be added and if desirable a fragrance material may also be included. To cleanse the skin, the composition is applied and massaged gently, and may be applied before or after bathing to provide a refreshing and soothing effect.

3 Claims, No Drawings

COSMETIC COMPOSITION AND METHOD OF MAKING THE SAME

This is a continuation-in-part application of my co-pending Application Ser. No. 21,551 filed Mar. 19, 1979 entitled Cosmetic Composition, now U.S. Pat. No. 4,255,452.

The present invention relates to a cosmetic composition and method of making same, and particularly to a cream preparation for cleansing, smoothing and moisturizing the skin.

An object of the invention is to provide a new and improved composition for cleansing, smoothing and moisturizing the skin.

Another object of the invention is to provide a new and improved method for making a cosmetic preparation which is inexpensive and readily accomplished.

The cosmetic composition according to the present invention contains as the major components a mixture of waer, non-fat dry milk solids, witch hazel, and olive oil. An emollient such as polyoxyethylene and a preservative such as methylparaben may be added, and if desired a fragrance material may also be included.

More particularly, the composition may contain 25 to 35 parts by weight of non-fat dry milk solids, 15 to 25 parts by weight of witch hazel, 35 to 45 parts by weight of olive oil, and 150 to 200 parts by weight of water. In the preferred form, the composition also includes 8 to 12 parts by weight of methylparaben, and 1 to 2 parts by weight of polyoxyethylene such as embodied in Product No. T21-0110 distributed by Technicon Instrument Corporation of Tarrytown, New York 10591. Technicon Instrument Corporation Product No. T21-0110 is polyoxyethylene sold to Technicon Instrument Corporation by ICI America under the trademark BRIJ-35. Polyoxyethylene available under the trademark BRIJ-35 has an average hydroxyl number of from about 40 to about 60. If desired 0.005 to 0.02 parts by weight of a fragrance material may be included.

The composition is prepared by thoroughly mixing with water by agitation at room temperature the witch hazel, and non-fat dry milk solids. Methylparaben and polyoxyethylene are each separately mixed with water and also added to the mixture. The olive oil is then slowly mixed into the mixture by gentle agitation at room temperature. A fragrance material may also be added at this time. The resulting mixture solidifies to a cream texture and consistancy at room temperature.

As an example, a composition in accordance with the invention was made by the method of the invention utilizing about, 150 to 200 parts by weight water, 30 parts by weight non-fat dry milk solids, 20 parts by weight witch hazel, 40 parts by weight olive oil, 9.5 parts by weight methylparaben, 1.5 parts by weight polyoxethylene, and 0.01 parts by weight fragrance. The composition was used by applying it to the skin and massaging gently. The composition may be used before or after bathing to provide a freshing and soothing effect. The composition may be applied to the entire body for leaving the skin soft, smooth and relaxed.

While certain proportions of the ingredients have been disclosed for preferred formulations, it should be understood that it is not intended that the scope of the invention be limited thereto, since it will be readily evident to those skilled in the art that various modifications can be made in the composition and method without substantially departing from the spirit of the invention.

What is claimed is:

1. A composition for topical application to the body consisting essentially of a mixture of about 25 to 35 parts by weight, non-fat dry milk solids, about 15 to 25 parts by weight witch hazel, about 35 to 45 parts by weight olive oil, about 150 to 200 parts by weight water and about 1 to 2 parts by weight polyoxyethylene having a hydroxyl number of from about 40 to about 60.

2. The composition of claim 1 which the mixture also includes about 8 to 12 parts by weight methylparaben.

3. The composition of claim 2 in which the mixture contains about 175 parts water, about 30 parts non-fat dry milk solids, about 20 parts witch hazel, about 40 parts olive oil, about 9 parts methylparaben, about 1.5 parts polyoxyethylene, all parts being by weight.

* * * * *

UNITED STATES PATENT AND TRADEMARK OFFICE
CERTIFICATE OF CORRECTION

PATENT NO. : 4,395,424
DATED : July 26, 1983
INVENTOR(S) : Ruby G. Veney

It is certified that error appears in the above-identified patent and that said Letters Patent are hereby corrected as shown below:

In column 1, line 21, "waer" should read -water-.

Signed and Sealed this

Thirtieth Day of October 1984

[SEAL]

Attest:

GERALD J. MOSSINGHOFF

*Attesting Officer*  *Commissioner of Patents and Trademarks*